United States Patent
Retsina et al.

(10) Patent No.: US 11,236,371 B2
(45) Date of Patent: Feb. 1, 2022

(54) PROCESSES FOR FERMENTATION OF LIGNOCELLULOSIC GLUCOSE TO ALIPHATIC ALCOHOLS OR ACIDS

(71) Applicant: GranBio Intellectual Property Holdings, LLC, Minnetrista, MN (US)

(72) Inventors: Theodora Retsina, Atlanta, GA (US); Vesa Pylkkanen, Atlanta, GA (US)

(73) Assignee: GranBio Intellectual Property Holdings, LLC, Atlanta, GA (US)

( * ) Notice: Subject to any disclaimer, the term of this patent is extended or adjusted under 35 U.S.C. 154(b) by 244 days.

(21) Appl. No.: 16/452,659

(22) Filed: Jun. 26, 2019

(65) Prior Publication Data

US 2020/0056213 A1    Feb. 20, 2020

Related U.S. Application Data

(63) Continuation of application No. 15/202,943, filed on Jul. 6, 2016, now abandoned.

(60) Provisional application No. 62/189,750, filed on Jul. 8, 2015.

(51) Int. Cl.
   *C12P 7/62*    (2006.01)
   *C12P 7/04*    (2006.01)

(52) U.S. Cl.
   CPC  *C12P 7/62* (2013.01); *C12P 7/04* (2013.01); *C12P 2203/00* (2013.01)

(58) Field of Classification Search
   CPC ...... C12P 7/04; C12P 7/08; C12P 7/10; C12P 7/22; C12P 2201/00; C12P 2203/00
   See application file for complete search history.

(56) References Cited

U.S. PATENT DOCUMENTS

| | | | | |
|---|---|---|---|---|
| 8,030,039 B1* | 10/2011 | Retsina | .................. | C13K 13/00 435/161 |
| 2009/0155869 A1* | 6/2009 | Buelter | .................. | C12N 15/52 435/160 |
| 2012/0009632 A1* | 1/2012 | Retsina | ............... | C08B 37/0057 435/105 |

FOREIGN PATENT DOCUMENTS

| | | | | |
|---|---|---|---|---|
| WO | WO-2013162881 A1 * | 10/2013 | ............. | C08B 1/003 |
| WO | WO-2015009145 A1 * | 1/2015 | ............. | C12P 19/02 |
| WO | WO-2015137868 A1 * | 9/2015 | ............. | D21C 11/00 |

OTHER PUBLICATIONS

Hoffman et al. "Ethanol Production By Coupled Enzyme Fermentation and Continuous Saccharification of Cellulose. Using Membrane Cell-Recycling Systems" from Membranes and Membrane Processes Edited by E. Drioli, 1986, pp. 533-542 (Year: 1986).*
Ylitervo et al. "Continuous Ethanol Production with a Membrane Bioreactor at High Acetic Acid Concentrations" Membranes 2014, 4, 372-387 (Year: 2014).*
Choudhury et al. "Lactic Acid Fermentation in Cell-Recycle Membrane Bioreactor" Applied Biochemistry and Biotechnology vol. 128, 2006, p. 171-183 (Year: 2006).*

* cited by examiner

*Primary Examiner* — Thane Underdahl
(74) *Attorney, Agent, or Firm* — O'Connor & Company; Ryan P. O'Connor (57) ABSTRACT

A process for producing an organic aliphatic product (such as butanol) from lignocellulosic biomass is provided, comprising: (a) fractionating lignocellulosic biomass in the presence of a solvent for lignin, a hydrolysis catalyst, and water, to produce a liquor containing hemicellulose, cellulose-rich solids, and lignin; (b) washing the cellulose-rich solids and separating the cellulose-rich solids from the liquor; (c) enzymatically hydrolyzing the cellulose-rich solids to generate a hydrolysate comprising glucose; (d) detoxifying the hydrolysate by neutralizing the hydrolysate, removing insoluble solids, and removing or oxidizing residual hydrolysis catalyst, thereby generating a purified hydrolysate; (e) fermenting the purified hydrolysate using a suitable microorganism to produce a dilute organic aliphatic product, wherein the microorganism is recycled with a membrane; (f) extracting the dilute organic aliphatic product into a water-immiscible extractant, to generate an intermediate material; and (g) distilling the intermediate material to generate a concentrated organic aliphatic product.

20 Claims, 1 Drawing Sheet

PROCESSES FOR FERMENTATION OF LIGNOCELLULOSIC GLUCOSE TO ALIPHATIC ALCOHOLS OR ACIDS

PRIORITY DATA

This patent application is a continuation application of U.S. patent application Ser. No. 15/202,943 filed Jul. 6, 2016, which claims priority to U.S. Provisional Patent App. No. 62/189,750, filed Jul. 8, 2015, each of which is hereby incorporated by reference herein.

FIELD

The present invention generally relates to fractionation processes for converting biomass into fermentable sugars, and conversion of the sugars to organic acids, alcohols (such as butanol), or other fermentation products. The invention also relates to process integration.

BACKGROUND

Biomass refining (or biorefining) is becoming more prevalent in industry. Cellulose fibers and sugars, hemicellulose sugars, lignin, syngas, and derivatives of these intermediates are being used by many companies for chemical and fuel production. Indeed, we now are observing the commercialization of integrated biorefineries that are capable of processing incoming biomass much the same as petroleum refineries now process crude oil. Underutilized lignocellulosic biomass feedstocks have the potential to be much cheaper than petroleum, on a carbon basis, as well as much better from an environmental life-cycle standpoint.

Lignocellulosic biomass is the most abundant renewable material on the planet and has long been recognized as a potential feedstock for producing chemicals, fuels, and materials. Lignocellulosic biomass normally comprises primarily cellulose, hemicellulose, and lignin. Cellulose and hemicellulose are natural polymers of sugars, and lignin is an aromatic/aliphatic hydrocarbon polymer reinforcing the entire biomass network. Some forms of biomass (e.g., recycled materials) do not contain hemicellulose.

Lignocellulosic biomass presents the vast majority of the sustainable feedstock for sugar-based fermentation. Lignocellulosics include woody and herbaceous material, and residues left behind after forestry and agricultural harvesting and processing. Biomass utilization for sugar recovery is hindered by its recalcitrant nature, resisting deconstruction by most chemicals and microorganisms. Even if the sugars are extracted, they come in a mixture of pentoses and hexoses. Most microorganisms can only utilize hexose sugars, or perform poorly on pentose conversion. Furthermore, the degradation products from harsh pretreatment, or the pretreatment chemicals themselves, are normally toxic to the microorganisms. These impurities can limit the conversion yield, selectivity, and productivity.

There are many reasons why it would be beneficial to process biomass in a way that effectively separates the major fractions (cellulose, hemicellulose, and lignin) from each other. Cellulose from biomass can be used in industrial cellulose applications directly, such as to make paper or other pulp-derived products. The cellulose can also be subjected to further processing to either modify the cellulose in some way or convert it into glucose. Hemicellulose sugars can be fermented to a variety of products, such as ethanol, or converted to other chemicals. Lignin from biomass has value as a solid fuel and also as an energy feedstock to produce liquid fuels, synthesis gas, or hydrogen; and as an intermediate to make a variety of polymeric compounds. Additionally, minor components such as proteins or rare sugars can be extracted and purified for specialty applications.

In light of this objective, a major shortcoming of previous process technologies is that one or two of the major components can be economically recovered in high yields, but not all three. Either the third component is sacrificially degraded in an effort to produce the other two components, or incomplete fractionation is accomplished. An important example is traditional biomass pulping (to produce paper and related goods). Cellulose is recovered in high yields, but lignin is primarily consumed by oxidation and hemicellulose sugars are mostly degraded. Approximately half of the starting biomass is essentially wasted in this manufacturing process. State-of-the-art biomass-pretreatment approaches typically can produce high yields of hemicellulose sugars but suffer from moderate cellulose and lignin yields.

There are several possible pathways to convert biomass into intermediates. One thermochemical pathway converts the feedstock into syngas (CO and $H_2$) through gasification or partial oxidation. Another thermochemical pathway converts biomass into liquid bio-oils through pyrolysis and separation. These are both high-temperature processes that intentionally destroy sugars in biomass.

Sugars (e.g., glucose and xylose) are desirable platform molecules because they can be fermented to a wide variety of fuels and chemicals, used to grow organisms or produce enzymes, converted catalytically to chemicals, or recovered and sold to the market. To recover sugars from biomass, the cellulose and/or the hemicellulose in the biomass must be hydrolyzed into sugars. This is a difficult task because lignin and hemicelluloses are bound to each other by covalent bonds, and the three components are arranged inside the fiber wall in a complex manner. This recalcitrance explains the natural resistance of woody biomass to decomposition, and explains the difficulty to convert biomass to sugars at high yields.

Fractionation of biomass into its principle components (cellulose, hemicellulose, and lignin) has several advantages. Fractionation of lignocellulosics leads to release of cellulosic fibers and opens the cell wall structure by dissolution of lignin and hemicellulose between the cellulose microfibrils. The fibers become more accessible for hydrolysis by enzymes. When the sugars in lignocellulosics are used as feedstock for fermentation, the process to open up the cell wall structure is often called "pretreatment." Pretreatment can significantly impact the production cost of lignocellulosic ethanol.

One of the most challenging technical obstacles for cellulose has been its recalcitrance towards hydrolysis for glucose production. Because of the high quantity of enzymes typically required, the enzyme cost can be a tremendous burden on the overall cost to turn cellulose into glucose for fermentation. Cellulose can be made to be reactive by subjecting biomass to severe chemistry, but that would jeopardize not only its integrity for other potential uses but also the yields of hemicellulose and lignin.

Many types of pretreatment have been studied. A common chemical pretreatment process employs a dilute acid, usually sulfuric acid, to hydrolyze and extract hemicellulose sugars and some lignin. A common physical pretreatment process employs steam explosion to mechanically disrupt the cellulose fibers and promote some separation of hemicellulose and lignin. Combinations of chemical and physical pretreatments are possible, such as acid pretreatment coupled with mechanical refining. It is difficult to avoid degradation of sugars. In some cases, severe pretreatments (i.e., high temperature and/or low pH) intentionally dehydrate sugars to furfural, levulinic acid, and related chemicals. Also, in common acidic pretreatment approaches, lignin handling is very problematic because acid-condensed lignin precipitates and forms deposits on surfaces throughout the process.

One type of pretreatment that can overcome many of these disadvantages is called "organosolv" pretreatment. Organosolv refers to the presence of an organic solvent for lignin, which allows the lignin to remain soluble for better lignin handling. Traditionally, organosolv pretreatment or pulping has employed ethanol-water solutions to extract most of the lignin but leave much of the hemicellulose attached to the cellulose. For some market pulps, it is acceptable or desirable to have high hemicellulose content in the pulp. When high sugar yields are desired, however, there is a problem. Traditional ethanol/water pulping cannot give high yields of hemicellulose sugars because the timescale for sufficient hydrolysis of hemicellulose to monomers causes soluble-lignin polymerization and then precipitation back onto cellulose, which negatively impacts both pulp quality as well as cellulose enzymatic digestibility.

An acid catalyst can be introduced into organosolv pretreatment to attempt to hydrolyze hemicellulose into monomers while still obtaining the solvent benefit. Conventional organosolv wisdom dictates that high delignification can be achieved, but that a substantial fraction of hemicellulose must be left in the solids because any catalyst added to hydrolyze the hemicellulose will necessarily degrade the sugars (e.g., to furfural) during extraction of residual lignin.

Contrary to the conventional wisdom, it has been found that fractionation with a solution of ethanol (or another solvent for lignin), water, and sulfur dioxide ($SO_2$) can simultaneously achieve several important objectives. The fractionation can be achieved at modest temperatures (e.g., 120-160° C.). The $SO_2$ can be easily recovered and reused. This process is able to effectively fractionation many biomass species, including softwoods, hardwoods, agricultural residues, and waste biomass. The $SO_2$ hydrolyzes the hemicelluloses and reduces or eliminates troublesome lignin-based precipitates. The presence of ethanol leads to rapid impregnation of the biomass, so that neither a separate impregnation stage nor size reduction smaller than wood chips are needed, thereby avoiding electricity-consuming sizing operations. The dissolved hemicelluloses are neither dehydrated nor oxidized (Iakovlev, "$SO_2$-ethanol-water fractionation of lignocellulosics," Ph.D. Thesis, Aalto Univ., Espoo, Finland, 2011). Cellulose, protected by the solvent, is fully retained in the solid phase and can subsequently be hydrolyzed to glucose. The mixture of hemicellulose monomer sugars and cellulose-derived glucose may be used for production of biofuels and chemicals.

Commercial sulfite pulping has been practiced since 1874. The focus of sulfite pulping is the preservation of cellulose. In an effort to do that, industrial variants of sulfite pulping take 6-10 hours to dissolve hemicelluloses and lignin, producing a low yield of fermentable sugars. Stronger acidic cooking conditions that hydrolyze the hemicellulose to produce a high yield of fermentable sugars also hydrolyze the cellulose, and therefore the cellulose is not preserved.

The dominant pulping process today is the Kraft process. Kraft pulping does not fractionate lignocellulosic material into its primary components. Instead, hemicellulose is degraded in a strong solution of sodium hydroxide with or without sodium sulfide. The cellulose pulp produced by the Kraft process is high quality, essentially at the expense of both hemicellulose and lignin.

Sulfite pulping produces spent cooking liquor termed sulfite liquor. Fermentation of sulfite liquor to hemicellulosic ethanol has been practiced primarily to reduce the environmental impact of the discharges from sulfite mills since 1909. However, ethanol yields do not exceed one-third of the original hemicellulose component. Ethanol yield is low due to the incomplete hydrolysis of the hemicelluloses to fermentable sugars and further compounded by sulfite pulping side products, such as furfural, methanol, acetic acid, and others fermentation inhibitors.

Solvent cooking chemicals have been attempted as an alternative to Kraft or sulfite pulping. The original solvent process is described in U.S. Pat. No. 1,856,567 by Kleinert et al. Groombridge et al. in U.S. Pat. No. 2,060,068 showed that an aqueous solvent with sulfur dioxide is a potent delignifying system to produce cellulose from lignocellulosic material. Three demonstration facilities for ethanol-water (Alcell), alkaline sulfite with anthraquinone and methanol (ASAM), and ethanol-water-sodium hydroxide (Organocell) were operated briefly in the 1990s.

In view of the state of the art, what is desired is to efficiently fractionate any lignocellulosic-based biomass (including, in particular, softwoods) into its primary components so that each can be used in potentially distinct processes. While not all commercial products require pure forms of cellulose, hemicellulose, or lignin, a platform biorefinery technology that enables processing flexibility in downstream optimization of product mix, is particularly desirable. An especially flexible fractionation technique would not only separate most of the hemicellulose and lignin from the cellulose, but also render the cellulose highly reactive to cellulase enzymes for the manufacture of fermentable glucose.

Often the rate-limiting step of fermentation is that the product itself inhibits the microorganism (e.g., Clostridium) productivity. Furthermore, the fermentation is normally done in a batch process, charging new microorganisms to each batch of sugars. Using membrane technology developed by Toray Industries of Japan, the fermented solvents can be passed through a membrane, where the Clostridium is recycled back to the fermenter and the products are sent to downstream purification. Continuous membrane-assisted fermentation enables many fold volumetric productivity enhancement, reducing the cost of fermentors.

Liquid-liquid extraction has been used to recover solutes that have strong solubility into the extractant. Concentrated solute is recovered from the extractant. The liquid-liquid extraction can significantly reduce the energy consumption, compared to traditional distillation. Energy integration and heat recovery can further reduce the energy consumption—making it even less than traditional ethanol production.

SUMMARY

The present invention addresses the aforementioned needs in the art.

Some variations provide a process for producing an organic aliphatic product from lignocellulosic biomass, the process comprising:

(a) fractionating a feedstock comprising lignocellulosic biomass in the presence of a solvent for lignin, a hydrolysis catalyst, and water, to produce a liquor containing hemicellulose, cellulose-rich solids, and lignin;

(b) washing the cellulose-rich solids and separating the cellulose-rich solids from the liquor;

(c) enzymatically hydrolyzing the cellulose-rich solids to generate a hydrolysate comprising glucose;

(d) detoxifying the hydrolysate by neutralizing the hydrolysate, removing insoluble solids, and removing or oxidizing residual hydrolysis catalyst, thereby generating a purified hydrolysate;

(e) fermenting the purified hydrolysate using a suitable microorganism in a fermentor to produce a dilute organic aliphatic product, wherein the microorganism is recycled with a membrane;

(f) extracting the dilute organic aliphatic product into a water-immiscible extractant, to generate an intermediate organic aliphatic product; and (g) distilling the intermediate organic aliphatic product to generate a concentrated organic aliphatic product.

The water-immiscible extractant may be selected from the group consisting of methyl ethyl ketone, methyl isobutyl ketone, decanol, dodecanol, oleyl alcohol, butyl butyrate, propionic acid, butyric acid, levulinic acid, succinic acid, and combinations thereof.

The organic aliphatic product is selected from $C_2$-$C_{12}$ linear or branched alcohols, $C_2$-$C_{12}$ linear or branched acids, $C_2$-$C_{12}$ linear or branched hydrocarbons, and isomers, derivatives, or reaction products, and combinations thereof.

In some embodiments, the organic aliphatic product includes an organic acid selected from the group consisting of formic acid, acetic acid, oxalic acid, lactic acid, propionic acid, 3-hydroxypropionic acid, malonic acid, aspartic acid, fumaric acid, malic acid, succinic acid, glutaric acid, adipic acid, citric acid, itaconic acid, levulinic acid, ascorbic acid, gluconic acid, kojic acid, threonine, glutamic acid, proline, lysine, alanine, serine, and any isomers, derivatives, or combinations thereof.

In some embodiments, the organic aliphatic product includes an oxygenated compound selected from the group consisting of ethanol, propanol, isopropanol, butanol, pentanol, hexanol, heptanol, octanol, glycerol, sorbitol, propanediol, butanediol, butanetriol, pentanediol, hexanediol, acetone, acetoin, butyrolactone, 3-hydroxybutyrolactone, and any isomers, derivatives, or combinations thereof.

In some embodiments, the solvent for lignin comprises an $C_1$-$C_8$ aliphatic or aromatic alcohol, comprises an aliphatic or aromatic hydrocarbon, an organic acid, an inorganic acid, an ionic liquid, or a combination thereof.

In some embodiments, the hydrolysis catalyst in step (a) is selected from the group consisting of sulfur dioxide, sulfur trioxide, sulfurous acid, sulfuric acid, sulfonic acid, lignosulfonic acid, elemental sulfur, polysulfides, and combinations or derivatives thereof. Preferably, the hydrolysis catalyst is sulfur dioxide. The hydrolysis catalyst may be present in a liquid-phase concentration of about 1 wt % to about 50 wt % during step (a).

In some embodiments, step (b) includes countercurrent washing of the cellulose-rich solids to remove the solvent for lignin, the lignin, and the hemicellulose.

In some embodiments, in step (e), the membrane is configured to bleed microorganisms to control cell density in the fermentor. Optionally, fresh microorganisms are propagated into the fermentor along with a nutrient supply to the fermentor.

Steps (f) and (g) may be integrated to improve heat recovery.

In some embodiments, step (g) includes recycling distillation bottoms containing enzymes back to step (c).

The process may further comprise hydrolyzing the hemicellulose contained in the liquor to produce hemicellulosic monomers.

Process integration including pinch analysis and energy optimization may be performed for each step in the process.

DETAILED DESCRIPTION OF SOME EMBODIMENTS

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing parameters, reaction conditions, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

This disclosure describes processes and apparatus to efficiently fractionate any lignocellulosic-based biomass into its primary major components (cellulose, lignin, and hemicellulose) so that each can be used in potentially distinct processes. The present invention, in some variations, is premised on the recognition that the AVAP® process (which is commonly owned with the assignee of this application) may be modified for the economic production of a wide variety of sugar-derived products, including products having a higher normal boiling point than water.

This invention provides an integrated biorefinery process, wherein lignocellulosic material is converted to aliphatic solutes via fermentation, preferably with microorganism recycle, and an extraction of the products. In particular, alcohol sulfite pretreatment is applied to produce cellulosic sugars, which are very low in hemicellulosic sugars. The cellulosic sugars may be detoxified and fermented together or separately with hemicellulosic sugars with suitable microorganisms, using membrane-assisted recycle. The products may be separated in liquid-liquid extraction from the fermentation broth.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only.

The present inventors have developed an integrated biorefinery process, where alcohol and sulfur dioxide are used to dissolve efficiently lignin and hemicelluloses, while leaving cellulose fibers nearly intact. The cooked material is preferably washed countercurrently to remove alcohol, lignin, and dissolved hemicelluloses, while the remaining cellulose is further enzymatically saccharified to high-purity glucose sugars. These glucose sugars are cleaned of cooking chemicals and solid impurities, before fermenting with a microorganism, which is recycled. Surprisingly, lowering the ethanol content reduces the hemicellulose content to below 2% by weight. After filtration, the high-purity glucose sugars are comparable to dextrose sugars, which are used for fermentation with most industrial microorganisms. The aliphatic organic products are extracted into a water-immiscible extractant, and further separated by distillation.

Figure 1:
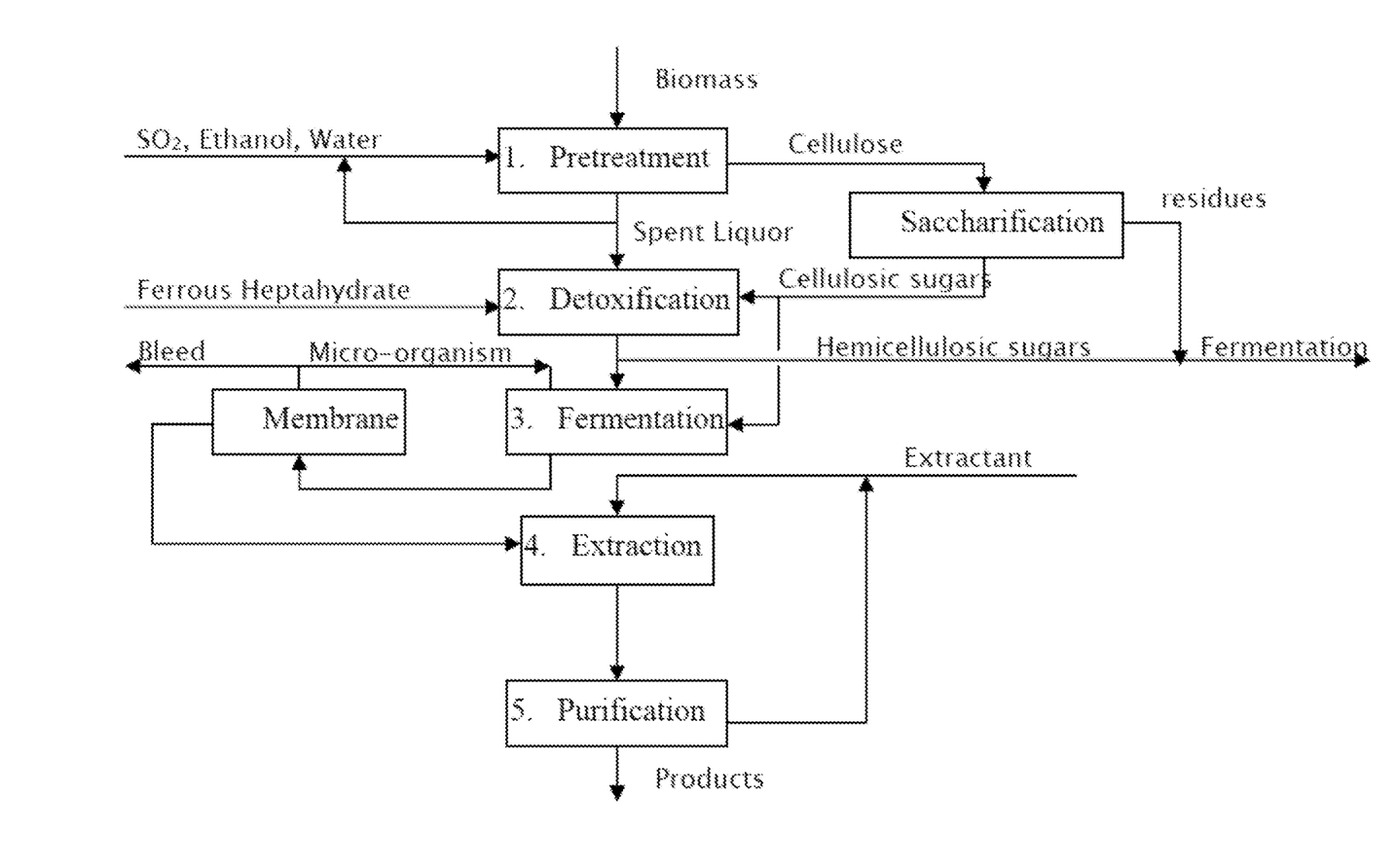
FIG. 1 illustrates a flow-sheet example of a biorefinery process according to the present invention, noting that the process steps may be in other sequences.

See FIG. 1 for an exemplary process, according to some embodiments. A biorefinery process is provided to convert lignocellulosic material into alcohol product and lignin derivatives through cooking of lignocellulosic material with alcohol, water, and sulfur dioxide, the following steps.

The first process step is pretreatment, element 1 in FIG. 1. Typical alcohol, water, and sulfur dioxide ratios by weight are between 10 and 80% of alcohol in water, and 9 50% of sulfur dioxide; preferably 22% alcohol, 68% water, and 12% sulfur dioxide by weight. Lignocellulosic material is cooked at a temperature from 95° C. to 170° C. for 10 minutes or more. The spent liquor consisting mainly of lignin and hemicellulosic sugars is removed from the cellulose fibers by filtration. The washed cellulose is saccharified with enzymes. Hemicelluloses are removed of cooking chemicals.

The second process step is detoxification of the hydrolyzates. This step includes neutralization, removal of solids, and catalytic oxidation of the remaining sulfur dioxide. The neutralization is preferably done with calcium oxide, magnesium oxide, ammonia or with hydrous solution thereof. The undissolved solids are filtered out to enable microorganism recycle. The catalytic oxidation may be done with hydrogen peroxide or ferrous sulfate heptahydrate as taught by Van Heiningen et al. in PCT patent publication WO2012123644, which is hereby incorporated by reference herein. The cellulosic sugars may be filtered from insolubles and evaporated to a syrup. The cellulosic sugars containing mostly glucose may be fermented separately from hemicellulosic sugars, if the fermentation organism prefers a single sugar over a mixture.

The third process step is fermentation with a membrane-assisted recycle of the microorganisms, wherein cellulosic sugars are converted to products. The products may include n-butanol from genetically modified yeast, or a mixture of acetone, n-butanol and ethanol from Clostridia family bacteria, or a mixture of isopropanol, n-butanol and ethanol from Clostridia bacteria. In some embodiments, a genetically modified Clostridium may include an isopropanol gene that has been cloned by transferring adh gene (which catalyzes the reduction of acetone to isopropanol) from another organism, which may be a different Clostridium or an *E-coli*, for example.

Other potential fermentation products include isomers of propanol, butanol, and pentanol, and/or organic aliphatic acids from naturally occurring and genetically modified organisms. Hemicellulosic sugars may be added to increase production or, fermented separately. In various embodiments, the fermentation product is selected from $C_2$-$C_{12}$ linear or branched alcohols, $C_2$-$C_{12}$ linear or branched acids, $C_2$-$C_{12}$ linear or branched hydrocarbons, or isomers, derivatives, or reaction products thereof, or combinations of any of the foregoing.

The fermentation products are preferably passed through a membrane, wherein the microorganism will be recycled back to the fermentor and the products sent to downstream purification. The membrane recycle system preferably is configured to bleed microorganisms to control cell density in the fermentor. Additionally, fresh microorganisms may be propagated into the fermentor along with nutrition supply.

The fourth process step is extraction of the solvents. A liquid-liquid extraction is used to concentrate dilute fermentation products to reduce energy requirements, as compared to the traditional distillation methods. Energy integration and heat recovery, using one or more principles described in detail hereinbelow, further reduce the energy consumption—making recovery more efficient than traditional ethanol distillation at high broth concentration. Thus, the process can be self-sufficient in thermal and electrical consumption by combusting biomass lignin and the process residues. The extractant is a water-immiscible solvent, such as methyl ethyl ketone, methyl isobutyl ketone, dodecanol, or mixture of extractants such as decanol in oleyl alcohol. The preferred extractant one or more aldol acids such as propionic, butyric, levulinic, or succinic acid, or butyl butyrate.

The fifth process step is purification, wherein solutes are separated from extractant by distillation. The distillation is performed with indirect steam to remove more volatile solutes from the extractant. If necessary, the solutes are separated and purified in fractional distillation columns. This step may also be practiced separately from the hemicellulosic product distillation. Optionally, distillation is practiced at low temperature, enabling part of the distillation bottoms containing yeast and enzymes to be recycled back to the enzymatic hydrolysis step.

The alcohol purification step may be combined with the extraction step to improve heat recovery. The bottoms of the fermentation may be sent to the evaporator to recover unfermentable solids for energy generation or other uses.

In some variations, the invention provides a process for fractionating lignocellulosic biomass into cellulose, hemicellulose, and lignin, the process comprising:

(a) in a digestor, fractionating a feedstock comprising lignocellulosic biomass in the presence of a solvent for lignin, sulfur dioxide, and water, to produce a liquor containing hemicellulose, cellulose-rich solids, and lignin;

(b) substantially separating the cellulose-rich solids from the liquor;

(c) hydrolyzing the hemicellulose contained in the liquor to produce hemicellulosic monomers;

(d) saccharifying at least some of the cellulose-rich solids to produce glucose;

(e) recovering the hemicellulosic monomers and the glucose, separately or in a combined stream, as fermentable sugars;

(f) fermenting at least a portion of the fermentable sugars to a fermentation product having a higher normal boiling point than water; and (g) recovering the fermentation product, wherein the process includes process integration of mass and/or energy between at least two of steps (a)-(g).

In preferred embodiments, the process integration includes pinch analysis and energy optimization one or more steps, preferably all steps, in the process.

In some embodiments, the process integration includes concentrating the fermentable sugars, recovering a condensate stream therefrom, and introducing the condensate stream to a fermentor feed stream and/or to a fermentor nutrient system.

In some embodiments, the process integration includes concentrating the fermentable sugars, recovering a condensate stream therefrom, and using the condensate stream for washing the cellulose-rich solids in step (b).

In some embodiments, the process integration includes sterilizing a fermentor or fermentor feed stream with a vapor take-off from one or more evaporators used for concentrating the fermentable sugars and/or one or more evaporators used for concentrating the fermentation product.

In some embodiments, the process integration includes pre-cooling a fermentor feed stream with a product stream comprising the fermentation product.

In some embodiments, the process integration includes concentrating the fermentation product in a non-externally-heated effect of a multiple-effect evaporation unit, such as the last effect of the multiple-effect evaporation unit.

In some embodiments, the process integration includes using vapor recompression and vacuum pumping to concentrate the fermentation product, to minimize cooling water requirements.

In some embodiments, the process integration includes concentrating one or more organic waste streams and combusting the one or more organic waste streams with lignin or another biomass-derived material.

In some embodiments, the process integration includes recovering the solvent for lignin that remains absorbed in cellulose-rich solids after step (b), by feeding one or more condensate streams and/or one or more waste streams to a stripping column.

In some embodiments, the process integration includes utilizing a rectifier reflux condensor to pre-evaporate stillage from a fermentation product distillation column. The process integration may also include preheating dimineralized water or preheating turbine condenser condensate, for example.

In some embodiments, the process integration includes integration of an evaporator associated with step (d), with a sulfur dioxide stripper and a beer column stillage evaporator.

The biomass feedstock may be selected from hardwoods, softwoods, forest residues, industrial wastes, pulp and paper wastes, consumer wastes, or combinations thereof. Some embodiments utilize agricultural residues, which include lignocellulosic biomass associated with food crops, annual grasses, energy crops, or other annually renewable feedstocks. Exemplary agricultural residues include, but are not limited to, corn stover, corn fiber, wheat straw, sugarcane bagasse, sugarcane straw, rice straw, oat straw, barley straw, miscanthus, energy cane straw/residue, or combinations thereof.

As used herein, "lignocellulosic biomass" means any material containing cellulose and lignin. Lignocellulosic biomass may also contain hemicellulose. Mixtures of one or more types of biomass can be used. In some embodiments, the biomass feedstock comprises both a lignocellulosic component (such as one described above) in addition to a sucrose-containing component (e.g., sugarcane or energy cane) and/or a starch component (e.g., corn, wheat, rice, etc.).

Various moisture levels may be associated with the starting biomass. The biomass feedstock need not be, but may be, relatively dry. In general, the biomass is in the form of a particulate or chip, but particle size is not critical in this invention.

The solvent for lignin preferably facilitates a higher mass transfer rate of the sulfur dioxide into the lignocellulosic biomass, compared to the mass transfer rate of sulfur dioxide into the lignocellulosic biomass with water alone. For example, ethanol facilitates better $SO_2$ mass transfer because ethanol (with dissolved $SO_2$) is able to penetrate into biomass pores more efficiently than water.

In some embodiments, the solvent for lignin comprises an oxygenated hydrocarbon, such as an aliphatic alcohol which may be a $C_1$-$C_8$ alcohol, for example, or an aromatic alcohol, such as phenol. In some embodiments, the solvent for lignin comprises an aliphatic or aromatic hydrocarbon.

In some embodiments, the solvent for lignin comprises an organic acid. For example, without limitation, the organic acid may be selected from the group consisting of acetic acid, formic acid, oxalic acid, lactic acid, propionic acid, 3-hydroxypropionic acid, malonic acid, aspartic acid, fumaric acid, malic acid, succinic acid, glutaric acid, adipic acid, citric acid, itaconic acid, levulinic acid, ascorbic acid, gluconic acid, kojic acid, and combinations thereof.

In these or other embodiments, the solvent for lignin comprises an inorganic acid, such as concentrated phosphoric acid. In certain embodiments, the solvent for lignin comprises an ionic liquid.

The process may further include recovering the lignin, lignosulfonates, or both of these. Recovery of lignin typically involves removal of solvent, dilution with water, adjustment of temperature or pH, addition of an acid or base, or some combination thereof.

The sulfur dioxide may be present in a liquid-phase concentration of about 1 wt % to about 50 wt % during step (a), or about 6 wt % to about 30 wt %, or about 9 wt % to about 20 wt %, in various embodiments.

Step (b) typically includes washing of the cellulose-rich solids, which preferably includes countercurrent washing of the cellulose-rich solids.

Hydrolyzing the hemicellulose contained in the liquor, in step (c), may be catalyzed by lignosulfonic acids that are generated during step (a).

The fermentation product may include an organic acid, such as (but not limited to) organic acids selected from the group consisting of formic acid, acetic acid, oxalic acid, lactic acid, propionic acid, 3-hydroxypropionic acid, malonic acid, aspartic acid, fumaric acid, malic acid, succinic acid, glutaric acid, adipic acid, citric acid, itaconic acid, levulinic acid, ascorbic acid, gluconic acid, kojic acid, threonine, glutamic acid, proline, lysine, alanine, serine, and any isomers, derivatives, or combinations thereof. In certain embodiments, the organic acid is succinic acid. "Derivatives" may be salts of these acids, or esters, or reaction products to convert the acid to another molecule that is not an acid. For example, when the fermentation product is succinic acid, it may be further converted to 1,4-butanediol as a derivative using known hydrotreating chemistry.

The fermentation product may include an oxygenated compound, such as (but not limited to) oxygenated compounds selected from the group consisting of ethanol, propanol, butanol, pentanol, hexanol, heptanol, octanol, glycerol, sorbitol, propanediol, butanediol, butanetriol, pentanediol, hexanediol, acetone, acetoin, butyrolactone, 3-hydroxybutyrolactone, and any isomers, derivatives, or combinations thereof.

In some embodiments, the oxygenated compound is a $C_3$ or higher alcohol or diol, such as 1-butanol, isobutanol, 1,4-butanediol, 2,3-butanediol, or mixtures thereof.

The fermentation product may include a hydrocarbon, such as isoprene, farnasene, and related compounds.

Multiple fermentation products may be produced in a single fermentor, in co-product production or as a result of byproducts due to contaminant microorganisms. For example, during fermentation to produce lactic acid, ethanol is a common byproduct due to contamination (and vice-versa).

Multiple fermentation products may be produced in separate fermentors. In some embodiments, a first fermentation product, such as an organic acid, is produced from glucose (hydrolyzed cellulose) while a second fermentation product, such as ethanol, is produced from hemicellulose sugars. Or, in some embodiments, different fermentations are directed to portions of feedstock having varying particle size, crystallinity, or other properties.

In some embodiments, different fermentations are directed to portions of whole biomass that is separated into a starch or sucrose-rich fraction, and a cellulose-rich fraction (for example, corn starch/stover or sugarcane syrup/bagasse). For example, from raw corn, an organic acid or polyol may be produced from starch (hydrolyzed to glucose), the same or a different organic acid or polyol may be produced from cellulose (hydrolyzed to glucose), and ethanol may be produced from hemicellulose sugars. Many variations are possible, as will be recognized by a person skilled in the biorefinery art, in view of the present disclosure.

The solvent for lignin may include a component that is the same as the fermentation product. In some embodiments, the solvent for lignin is the same compound as the fermentation product. For example, the solvent and the fermentation product may be 1-butanol, or lactic acid, succinic acid, or 1,4-butanediol. Of course, other solvents may be present even when these products are utilized as solvents or co-solvents. Beneficially, a portion of the fermentation product may be recycled to step (a) for use as the solvent for lignin.

In some embodiments, the fermentation product includes an enzymatically isomerized variant of at least a portion of the fermentable sugars. For example, the enzymatically isomerized variant may include fructose which is isomerized from glucose. In some embodiments, glucose, which is normally D-glucose, is isomerized with enzymes to produce L-glucose.

In some embodiments, the fermentation product includes one or more proteins, amino acids, enzymes, or microorganisms. Such fermentation products may be recovered and used within the process; for example, cellulase or hemicellulase enzymes may be used for hydrolyzing cellulose-rich solids or hemicellulose oligomers.

Some variations are premised on the recognition that the clean cellulose produced in these processes may be not only hydrolyzed to glucose, but also recovered as a cellulose pulp product, intermediate, or precursor (such as for nanocellulose). Also, the initial fractionation step (in the digestor) does not necessarily employ $SO_2$ as the hydrolysis catalyst, although $SO_2$ is a preferred hydrolysis catalyst. In some variations, a process for fractionating lignocellulosic biomass into cellulose, hemicellulose, and lignin comprises:

(a) in a digestor, fractionating a feedstock comprising lignocellulosic biomass feedstock in the presence of a solvent for lignin, a hydrolysis catalyst, and water, to produce a liquor containing hemicellulose, cellulose-rich solids, and lignin;

(b) substantially separating the cellulose-rich solids from the liquor;

(c) hydrolyzing the hemicellulose contained in the liquor to produce hemicellulosic monomers;

(d) recovering the hemicellulosic monomers as fermentable sugars;

(e) fermenting at least a portion of the fermentable sugars to a fermentation product having a higher normal boiling point than water; and (f) recovering the fermentation product, wherein the process includes process integration of mass and/or energy between at least two of steps (a)-(f).

In some embodiments, the hydrolysis catalyst is present in a liquid-phase concentration of about 1 wt % to about 50 wt % during step (a), such as about 6 wt % to about 30 wt %, or about 9 wt % to about 20 wt %. The hydrolysis catalyst in step (a) may be selected from the group consisting of sulfur dioxide, sulfur trioxide, sulfurous acid, sulfuric acid, sulfonic acid, lignosulfonic acid, elemental sulfur, polysulfides, and combinations or derivatives thereof.

In some embodiments, the hydrolyzing in step (c) utilizes the hydrolysis catalyst from step (a), or a reaction product thereof. For example, in certain embodiments the hydrolysis catalyst is sulfur dioxide and the reaction product is lignosulfonic acid. In other embodiments, the hydrolyzing in step (c) utilizes hemicellulase enzymes as hydrolysis catalyst.

In some embodiments, the solvent for lignin also contains the functionality of a hydrolysis catalyst, i.e. there is not a separate hydrolysis catalyst present. In particular, when the solvent for lignin is an organic acid, it may also function as the hydrolysis catalyst.

In some embodiments, the process further comprises saccharifying at least some of the cellulose-rich solids to produce glucose. In these or other embodiments, the process further comprises recovering or further treating or reacting at least some of the cellulose-rich solids as a pulp precursor or product. When glucose is produced (by acid or enzyme hydrolysis of the cellulose), that glucose may form part of the fermentable sugars, either separately from the hemicellulose-derived fermentable sugars, or as a combined sugar stream.

In some embodiments, the fermentation product is ethanol, 1-butanol, succinic acid, 1,4-butanediol, or a combination thereof. In some embodiments, the solvent for lignin includes a component that is the same as the fermentation product, or is the same compound as the fermentation product. Thus a portion of the fermentation product may be recycled to step (a) for use as the solvent for lignin.

Some variations provide a process for fractionating lignocellulosic biomass into cellulose, hemicellulose, and lignin, the process comprising:

(a) in a digestor, fractionating a feedstock comprising lignocellulosic biomass feedstock in the presence of a solvent for lignin, a hydrolysis catalyst, and water, to produce a liquor containing hemicellulose, cellulose-rich solids, and lignin;

(b) substantially separating the cellulose-rich solids from the liquor;

(c) hydrolyzing the hemicellulose contained in the liquor to produce hemicellulosic monomers;

(d) recovering the hemicellulosic monomers as fermentable sugars;

(e) fermenting at least a portion of the fermentable sugars to a fermentation product having a relative volatility with water of less than 1.0; and (f) recovering the fermentation product, wherein the process includes process integration of mass and/or energy between at least two of steps (a)-(f).

The relative volatility of the fermentation product with water may be calculated at any relevant temperature, such as 25° C. (i.e. ambient conditions), or at the temperature of the digestor in step (a), or at the temperature of recovering (e.g., distillation) in step (f). It should also be noted that the relative volatility of the fermentation product with water technically depends on the other components present in solution, due to multicomponent thermodynamic equilibria. It is possible that the ideal relative volatility of a product with water is greater (or less) than 1.0 at a given temperature, but that in actual solution, the relative volatility of the product with water is less (or greater) than 1.0.

In any of the embodiments described above, the process may further include hydrolying at least a portion of the cellulose-rich solids into glucose, and optionally fermenting the glucose to the fermentation product.

Some variations provide a process for fractionating lignocellulosic biomass into cellulose, hemicellulose, and lignin, the process comprising:

(a) in a digestor, fractionating a feedstock comprising lignocellulosic biomass feedstock in the presence of a solvent for lignin, a hydrolysis catalyst, and water, to produce a liquor containing hemicellulose, cellulose-rich solids, and lignin;

(b) hydrolyzing the hemicellulose contained in the liquor to produce hemicellulosic monomers;

(c) substantially separating the cellulose-rich solids from the liquor;

(d) recovering the hemicellulosic monomers as fermentable sugars;

(e) fermenting at least a portion of the fermentable sugars to a fermentation product having a relative volatility with water of less than 1.0; and (f) recovering the fermentation product, wherein the process includes process integration of mass and/or energy between at least two of steps (a)-(f), and wherein steps (a) and (b) are optionally combined in a single vessel.

Some variations provide a process for fractionating lignocellulosic biomass into cellulose, hemicellulose, and lignin, the process comprising:

(a) in a digestor, fractionating a feedstock comprising lignocellulosic biomass feedstock in the presence of a solvent for lignin, a hydrolysis catalyst, and water, to produce a liquor containing hemicellulose, cellulose-rich solids, and lignin;

(b) hydrolyzing the cellulose-rich solids to produce glucose;

(c) hydrolyzing the hemicellulose contained in the liquor to produce hemicellulosic monomers;

(d) recovering the glucose and the hemicellulosic monomers as fermentable sugars, separately or in a combined stream;

(e) fermenting at least a portion of the fermentable sugars to a fermentation product having a relative volatility with water of less than 1.0; and (f) recovering the fermentation product, wherein the process includes process integration of mass and/or energy between at least two of steps (a)-(f).

Reaction conditions and operation sequences may vary widely. Some embodiments employ conditions described in U.S. Pat. No. 8,030,039, issued Oct. 4, 2011; U.S. Pat. No. 8,038,842, issued Oct. 11, 2011; U.S. Pat. No. 8,268,125, issued Sep. 18, 2012; and U.S. patent application Ser. Nos. 13/004,431; 12/234,286; 13/585,710; 12/250,734; 12/397,284; 12/304,046; 13/500,916; 13/626,220; 12/854,869; 61/732,047; 61/735,738; 61/739,343; 61/747,010; 61/747,105; 61/747,376; 61/747,379; 61/747,382; and/or 61/747,408, including the prosecution histories thereof. Each of these commonly owned patent applications is hereby incorporated by reference herein in its entirety. In some embodiments, the process is a variation of the AVAP® process technology which is commonly owned with the assignee of this patent application.

In some embodiments, a first process step is "cooking" (equivalently, "digesting") which fractionates the three lignocellulosic material components (cellulose, hemicellulose, and lignin) to allow easy downstream removal. Specifically, hemicelluloses are dissolved and over 50% are completely hydrolyzed; cellulose is separated but remains resistant to hydrolysis; and part of the lignin is sulfonated into water-soluble lignosulfonates.

The lignocellulosic material is processed in a solution (cooking liquor) of aliphatic alcohol, water, and sulfur dioxide. The cooking liquor preferably contains at least 10 wt %, such as at least 20 wt %, 30 wt %, 40 wt %, or 50 wt % of a solvent for lignin. For example, the cooking liquor may contain about 30-70 wt % solvent, such as about 50 wt % solvent. The solvent for lignin may be an aliphatic alcohol, such as methanol, ethanol, 1-propanol, 2-propanol, 1-butanol, 2-butanol, isobutanol, 1-pentanol, 1-hexanol, or cyclohexanol. The solvent for lignin may be an aromatic alcohol, such as phenol or cresol. Other lignin solvents are possible, such as (but not limited to) glycerol, methyl ethyl ketone, or diethyl ether. Combinations of more than one solvent may be employed.

Preferably, enough solvent is included in the extractant mixture to dissolve the lignin present in the starting material. The solvent for lignin may be completely miscible, partially miscible, or immiscible with water, so that there may be more than one liquid phase. Potential process advantages arise when the solvent is miscible with water, and also when the solvent is immiscible with water. When the solvent is water-miscible, a single liquid phase forms, so mass transfer of lignin and hemicellulose extraction is enhanced, and the downstream process must only deal with one liquid stream. When the solvent is immiscible in water, the extractant mixture readily separates to form liquid phases, so a distinct separation step can be avoided or simplified. This can be advantageous if one liquid phase contains most of the lignin and the other contains most of the hemicellulose sugars, as this facilitates recovering the lignin from the hemicellulose sugars.

The cooking liquor preferably contains sulfur dioxide and/or sulfurous acid ($H_2SO_3$). The cooking liquor preferably contains $SO_2$, in dissolved or reacted form, in a concentration of at least 3 wt %, preferably at least 6 wt %, more preferably at least 8 wt %, such as about 9 wt %, 10 wt %, 11 wt %, 12 wt %, 13 wt %, 14 wt %, 15 wt %, 20 wt %, 25 wt %, 30 wt % or higher. The cooking liquor may also contain one or more species, separately from $SO_2$, to adjust the pH. The pH of the cooking liquor is typically about 4 or less.

Sulfur dioxide is a preferred acid catalyst, because it can be recovered easily from solution after hydrolysis. The majority of the $SO_2$ from the hydrolysate may be stripped and recycled back to the reactor. Recovery and recycling translates to less lime required compared to neutralization of comparable sulfuric acid, less solids to dispose of, and less separation equipment. The increased efficiency owing to the inherent properties of sulfur dioxide mean that less total acid or other catalysts may be required. This has cost advantages, since sulfuric acid can be expensive. Additionally, and quite significantly, less acid usage also will translate into lower costs for a base (e.g., lime) to increase the pH following hydrolysis, for downstream operations. Furthermore, less acid and less base will also mean substantially less generation of waste salts (e.g., gypsum) that may otherwise require disposal.

In some embodiments, an additive may be included in amounts of about 0.1 wt % to 10 wt % or more to increase cellulose viscosity. Exemplary additives include ammonia, ammonia hydroxide, urea, anthraquinone, magnesium oxide, magnesium hydroxide, sodium hydroxide, and their derivatives.

The cooking is performed in one or more stages using batch or continuous digestors. Solid and liquid may flow cocurrently or countercurrently, or in any other flow pattern that achieves the desired fractionation. The cooking reactor may be internally agitated, if desired.

Depending on the lignocellulosic material to be processed, the cooking conditions are varied, with temperatures from about 65° C. to 175° C., for example 75° C., 85° C., 95° C., 105° C., 115° C., 125° C., 130° C., 135° C., 140° C., 145° C., 150° C., 155° C., 165° C. or 170° C., and corresponding pressures from about 1 atmosphere to about 15 atmospheres in the liquid or vapor phase. The cooking time of one or more stages may be selected from about 15 minutes to about 720 minutes, such as about 30, 45, 60, 90, 120, 140, 160, 180, 250, 300, 360, 450, 550, 600, or 700 minutes. Generally, there is an inverse relationship between the temperature used during the digestion step and the time needed to obtain good fractionation of the biomass into its constituent parts.

The cooking liquor to lignocellulosic material ratio may be selected from about 1 to about 10, such as about 2, 3, 4, 5, or 6. In some embodiments, biomass is digested in a pressurized vessel with low liquor volume (low ratio of cooking liquor to lignocellulosic material), so that the cooking space is filled with ethanol and sulfur dioxide vapor in equilibrium with moisture. The cooked biomass is washed in alcohol-rich solution to recover lignin and dissolved hemicelluloses, while the remaining pulp is further processed. In some embodiments, the process of fractionating lignocellulosic material comprises vapor-phase cooking of lignocellulosic material with aliphatic alcohol (or other solvent for lignin), water, and sulfur dioxide. See, for example, U.S. Pat. Nos. 8,038,842 and 8,268,125 which are incorporated by reference herein.

A portion or all of the sulfur dioxide may be present as sulfurous acid in the extract liquor. In certain embodiments, sulfur dioxide is generated in situ by introducing sulfurous acid, sulfite ions, bisulfite ions, combinations thereof, or a salt of any of the foregoing. Excess sulfur dioxide, following hydrolysis, may be recovered and reused.

In some embodiments, sulfur dioxide is saturated in water (or aqueous solution, optionally with an alcohol) at a first temperature, and the hydrolysis is then carried out at a second, generally higher, temperature. In some embodiments, sulfur dioxide is sub-saturated. In some embodiments, sulfur dioxide is super-saturated. In some embodiments, sulfur dioxide concentration is selected to achieve a certain degree of lignin sulfonation, such as 1%, 2%, 3%, 4%, 5%, 6%, 7%, 8%, 9%, or 10% sulfur content. $SO_2$ reacts chemically with lignin to form stable lignosulfonic acids which may be present both in the solid and liquid phases.

The concentration of sulfur dioxide, additives, and aliphatic alcohol (or other solvent) in the solution and the time of cook may be varied to control the yield of cellulose and hemicellulose in the pulp. The concentration of sulfur dioxide and the time of cook may be varied to control the yield of lignin versus lignosulfonates in the hydrolysate. In some embodiments, the concentration of sulfur dioxide, temperature, and the time of cook may be varied to control the yield of fermentable sugars.

Once the desired amount of fractionation of both hemicellulose and lignin from the solid phase is achieved, the liquid and solid phases are separated. Conditions for the separation may be selected to minimize the reprecipitation of the extracted lignin on the solid phase. This is favored by conducting separation or washing at a temperature of at least the glass-transition temperature of lignin (about 120° C.).

The physical separation can be accomplished either by transferring the entire mixture to a device that can carry out the separation and washing, or by removing only one of the phases from the reactor while keeping the other phase in place. The solid phase can be physically retained by appropriately sized screens through which liquid can pass. The solid is retained on the screens and can be kept there for successive solid-wash cycles. Alternately, the liquid may be retained and solid phase forced out of the reaction zone, with centrifugal or other forces that can effectively transfer the solids out of the slurry. In a continuous system, countercurrent flow of solids and liquid can accomplish the physical separation.

The recovered solids normally will contain a quantity of lignin and sugars, some of which can be removed easily by washing. The washing-liquid composition can be the same as or different than the liquor composition used during fractionation. Multiple washes may be performed to increase effectiveness. Preferably, one or more washes are performed with a composition including a solvent for lignin, to remove additional lignin from the solids, followed by one or more washes with water to displace residual solvent and sugars from the solids. Recycle streams, such as from solvent-recovery operations, may be used to wash the solids.

After separation and washing as described, a solid phase and at least one liquid phase are obtained. The solid phase contains substantially undigested cellulose. A single liquid phase is usually obtained when the solvent and the water are miscible in the relative proportions that are present. In that case, the liquid phase contains, in dissolved form, most of the lignin originally in the starting lignocellulosic material, as well as soluble monomeric and oligomeric sugars formed in the hydrolysis of any hemicellulose that may have been present. Multiple liquid phases tend to form when the solvent and water are wholly or partially immiscible. The lignin tends to be contained in the liquid phase that contains most of the solvent. Hemicellulose hydrolysis products tend to be present in the liquid phase that contains most of the water.

In some embodiments, hydrolysate from the cooking step is subjected to pressure reduction. Pressure reduction may be done at the end of a cook in a batch digestor, or in an external flash tank after extraction from a continuous digestor, for example. The flash vapor from the pressure reduction may be collected into a cooking liquor make-up vessel. The flash vapor contains substantially all the unreacted sulfur dioxide which may be directly dissolved into new cooking liquor. The cellulose is then removed to be washed and further treated as desired.

A process washing step recovers the hydrolysate from the cellulose. The washed cellulose is pulp that may be used for various purposes (e.g., paper or nanocellulose production). The weak hydrolysate from the washer continues to the final reaction step; in a continuous digestor this weak hydrolysate may be combined with the extracted hydrolysate from the external flash tank. In some embodiments, washing and/or separation of hydrolysate and cellulose-rich solids is conducted at a temperature of at least about 100° C., 110° C., or 120° C. The washed cellulose may also be used for glucose production via cellulose hydrolysis with enzymes or acids.

In another reaction step, the hydrolysate may be further treated in one or multiple steps to hydrolyze the oligomers into monomers. This step may be conducted before, during, or after the removal of solvent and sulfur dioxide. The solution may or may not contain residual solvent (e.g. alcohol). In some embodiments, sulfur dioxide is added or allowed to pass through to this step, to assist hydrolysis. In these or other embodiments, an acid such as sulfurous acid or sulfuric acid is introduced to assist with hydrolysis. In some embodiments, the hydrolysate is autohydrolyzed by heating under pressure. In some embodiments, no additional acid is introduced, but lignosulfonic acids produced during the initial cooking are effective to catalyze hydrolysis of hemicellulose oligomers to monomers. In various embodiments, this step utilizes sulfur dioxide, sulfurous acid, sulfuric acid at a concentration of about 0.01 wt % to 30 wt %, such as about 0.05 wt %, 0.1 wt %, 0.2 wt %, 0.5 wt %, 1 wt %, 2 wt %, 5 wt %, 10 wt %, or 20 wt %. This step may be carried out at a temperature from about 100° C. to 220° C., such as about 110° C., 120° C., 130° C., 140° C., 150° C., 160° C., 170° C., 180° C., 190° C., 200° C., or 210° C. Heating may be direct or indirect to reach the selected temperature.

The reaction step produces fermentable sugars which can then be concentrated by evaporation to a fermentation feedstock. Concentration by evaporation may be accomplished before, during, or after the treatment to hydrolyze oligomers. The final reaction step may optionally be followed by steam stripping of the resulting hydrolysate to remove and recover sulfur dioxide and alcohol, and for removal of potential fermentation-inhibiting side products. The evaporation process may be under vacuum or pressure, from about –0.1 atmospheres to about 10 atmospheres, such as about 0.1 atm, 0.3 atm, 0.5 atm, 1.0 atm, 1.5 atm, 2 atm, 4 atm, 6 atm, or 8 atm.

Recovering and recycling the sulfur dioxide may utilize separations such as, but not limited to, vapor-liquid disengagement (e.g. flashing), steam stripping, extraction, or combinations or multiple stages thereof. Various recycle ratios may be practiced, such as about 0.1, 0.2, 0.3, 0.4, 0.5, 0.6, 0.7, 0.8, 0.9, 0.95, or more. In some embodiments, about 90-99% of initially charged $SO_2$ is readily recovered by distillation from the liquid phase, with the remaining 1-10% (e.g., about 3-5%) of the $SO_2$ primarily bound to dissolved lignin in the form of lignosulfonates.

In a preferred embodiment, the evaporation step utilizes an integrated alcohol stripper and evaporator. Evaporated vapor streams may be segregated so as to have different concentrations of organic compounds in different streams. Evaporator condensate streams may be segregated so as to have different concentrations of organic compounds in different streams. Alcohol may be recovered from the evaporation process by condensing the exhaust vapor and returning to the cooking liquor make-up vessel in the cooking step. Clean condensate from the evaporation process may be used in the washing step.

In some embodiments, an integrated alcohol stripper and evaporator system is employed, wherein aliphatic alcohol is removed by vapor stripping, the resulting stripper product stream is concentrated by evaporating water from the stream, and evaporated vapor is compressed using vapor compression and is reused to provide thermal energy.

The hydrolysate from the evaporation and final reaction step contains mainly fermentable sugars but may also contain lignin depending on the location of lignin separation in the overall process configuration. The hydrolysate may be concentrated to a concentration of about 5 wt % to about 60 wt % solids, such as about 10 wt %, 15 wt %, 20 wt %, 25 wt %, 30 wt %, 35 wt %, 40 wt %, 45 wt %, 50 wt % or 55 wt % solids. The hydrolysate contains fermentable sugars.

Fermentable sugars are defined as hydrolysis products of cellulose, galactoglucomannan, glucomannan, arabinoglucuronoxylans, arabinogalactan, and glucuronoxylans into their respective short-chained oligomers and monomer products, i.e., glucose, mannose, galactose, xylose, and arabinose. The fermentable sugars may be recovered in purified form, as a sugar slurry or dry sugar solids, for example. Any known technique may be employed to recover a slurry of sugars or to dry the solution to produce dry sugar solids.

In some embodiments, the fermentable sugars are fermented to produce biochemicals or biofuels such as (but by no means limited to) ethanol, isopropanol, acetone, 1-butanol, isobutanol, lactic acid, succinic acid, or any other fermentation products. Some amount of the fermentation product may be a microorganism or enzymes, which may be recovered if desired.

When the fermentation will employ bacteria, such as Clostridia bacteria, it is preferable to further process and condition the hydrolysate to raise pH and remove residual $SO_2$ and other fermentation inhibitors. The residual $SO_2$ (i.e., following removal of most of it by stripping) may be catalytically oxidized to convert residual sulfite ions to sulfate ions by oxidation. This oxidation may be accomplished by adding an oxidation catalyst, such as $FeSO4.7H_2O$, that oxidizes sulfite ions to sulfate ions, which is a well-known practice for fermentation to acetone/butanol/ethanol (ABE). Preferably, the residual $SO_2$ is reduced to less than about 100 ppm, 50 ppm, 25 ppm, 10 ppm, 5 ppm, or 1 ppm.

In some embodiments, the process further comprises recovering the lignin as a co-product. The sulfonated lignin may also be recovered as a co-product. In certain embodiments, the process further comprises combusting or gasifying the sulfonated lignin, recovering sulfur contained in the sulfonated lignin in a gas stream comprising reclaimed sulfur dioxide, and then recycling the reclaimed sulfur dioxide for reuse.

The process lignin separation step is for the separation of lignin from the hydrolysate and can be located before or after the final reaction step and evaporation. If located after, then lignin will precipitate from the hydrolysate since alcohol has been removed in the evaporation step. The remaining water-soluble lignosulfonates may be precipitated by converting the hydrolysate to an alkaline condition (pH higher than 7) using, for example, an alkaline earth oxide, preferably calcium oxide (lime). The combined lignin and lignosulfonate precipitate may be filtered. The lignin and lignosulfonate filter cake may be dried as a co-product or burned or gasified for energy production. The hydrolysate from filtering may be recovered and sold as a concentrated sugar solution product or further processed in a subsequent fermentation or other reaction step.

Native (non-sulfonated) lignin is hydrophobic, while lignosulfonates are hydrophilic. Hydrophilic lignosulfonates may have less propensity to clump, agglomerate, and stick to surfaces. Even lignosulfonates that do undergo some condensation and increase of molecular weight, will still have an $HSO_3$ group that will contribute some solubility (hydrophilic).

In some embodiments, the soluble lignin precipitates from the hydrolysate after solvent has been removed in the evaporation step. In some embodiments, reactive lignosulfonates are selectively precipitated from hydrolysate using excess lime (or other base, such as ammonia) in the presence of aliphatic alcohol. In some embodiments, hydrated lime is used to precipitate lignosulfonates. In some embodiments, part of the lignin is precipitated in reactive form and the remaining lignin is sulfonated in water-soluble form.

The process fermentation and distillation steps are intended for the production of fermentation products, such as alcohols or organic acids. After removal of cooking chemicals and lignin, and further treatment (oligomer hydrolysis), the hydrolysate contains mainly fermentable sugars in water solution from which any fermentation inhibitors have been preferably removed or neutralized. The hydrolysate is fermented to produce dilute alcohol or organic acids, from 1 wt % to 20 wt % concentration. The dilute product is distilled or otherwise purified as is known in the art.

When alcohol is produced, such as ethanol, some of it may be used for cooking liquor makeup in the process cooking step. Also, in some embodiments, a distillation column stream, such as the bottoms, with or without evaporator condensate, may be reused to wash cellulose. In some embodiments, lime may be used to dehydrate product alcohol. Side products may be removed and recovered from the hydrolysate. These side products may be isolated by processing the vent from the final reaction step and/or the condensate from the evaporation step. Side products include furfural, hydroxymethyl furfural (HMF), methanol, acetic acid, and lignin-derived compounds, for example.

The cellulose-rich material is highly reactive in the presence of industrial cellulase enzymes that efficiently break the cellulose down to glucose monomers. It has been found experimentally that the cellulose-rich material, which generally speaking is highly delignified, rapidly hydrolyzes to glucose with relatively low quantities of enzymes. For example, the cellulose-rich solids may be converted to glucose with at least 80% yield within 24 hours at 50° C. and 2 wt % solids, in the presence of a cellulase enzyme mixture in an amount of no more than 15 filter paper units (FPU) per g of the solids. In some embodiments, this same conversion requires no more than 5 FPU per g of the solids.

The glucose may be fermented to an alcohol, an organic acid, or another fermentation product. The glucose may be used as a sweetener or isomerized to enrich its fructose content. The glucose may be used to produce baker's yeast. The glucose may be catalytically or thermally converted to various organic acids and other materials.

In some embodiments, the cellulose-rich material is further processed into one more cellulose products. Cellulose products include market pulp, dissolving pulp (also known as α-cellulose), fluff pulp, purified cellulose, paper, paper products, and so on. Further processing may include bleaching, if desired. Further processing may include modification of fiber length or particle size, such as when producing nanocellulose or nanofibrillated or microfibrillated cellulose. It is believed that the cellulose produced by this process is highly amenable to derivatization chemistry for cellulose derivatives and cellulose-based materials such as polymers.

When hemicellulose is present in the starting biomass, all or a portion of the liquid phase contains hemicellulose sugars and soluble oligomers. It is preferred to remove most of the lignin from the liquid, as described above, to produce a fermentation broth which will contain water, possibly some of the solvent for lignin, hemicellulose sugars, and various minor components from the digestion process. This fermentation broth can be used directly, combined with one or more other fermentation streams, or further treated. Further treatment can include sugar concentration by evaporation; addition of glucose or other sugars (optionally as obtained from cellulose saccharification); addition of various nutrients such as salts, vitamins, or trace elements; pH adjustment; and removal of fermentation inhibitors such as acetic acid and phenolic compounds. The choice of conditioning steps should be specific to the target product(s) and microorganism(s) employed.

In some embodiments, hemicellulose sugars are not fermented but rather are recovered and purified, stored, sold, or converted to a specialty product. Xylose, for example, can be converted into xylitol.

A lignin product can be readily obtained from a liquid phase using one or more of several methods. One simple technique is to evaporate off all liquid, resulting in a solid lignin-rich residue. This technique would be especially advantageous if the solvent for lignin is water-immiscible. Another method is to cause the lignin to precipitate out of solution. Some of the ways to precipitate the lignin include (1) removing the solvent for lignin from the liquid phase, but not the water, such as by selectively evaporating the solvent from the liquid phase until the lignin is no longer soluble; (2) diluting the liquid phase with water until the lignin is no longer soluble; and (3) adjusting the temperature and/or pH of the liquid phase. Methods such as centrifugation can then be utilized to capture the lignin. Yet another technique for removing the lignin is continuous liquid-liquid extraction to selectively remove the lignin from the liquid phase, followed by removal of the extraction solvent to recover relatively pure lignin.

Lignin produced in accordance with the invention can be used as a fuel. As a solid fuel, lignin is similar in energy content to coal. Lignin can act as an oxygenated component in liquid fuels, to enhance octane while meeting standards as a renewable fuel. The lignin produced herein can also be used as polymeric material, and as a chemical precursor for producing lignin derivatives. The sulfonated lignin may be sold as a lignosulfonate product, or burned for fuel value.

The present invention also provides systems configured for carrying out the disclosed processes, and compositions produced therefrom. Any stream generated by the disclosed processes may be partially or completed recovered, purified or further treated, and/or marketed or sold.

Apparatus may be configured to carry out the processes disclosed. In some embodiments, a system may be assembled for fractionating lignocellulosic biomass into cellulose, hemicellulose, and lignin, the system comprising elements configured to optionally (i.e., when the system is operating) perform the steps of:

(a) in a digestor, fractionating a feedstock comprising lignocellulosic biomass feedstock in the presence of a solvent for lignin, a hydrolysis catalyst, and water, to produce a liquor containing hemicellulose, cellulose-rich solids, and lignin;

(b) substantially separating the cellulose-rich solids from the liquor;

(c) hydrolyzing the hemicellulose contained in the liquor to produce hemicellulosic monomers;

(d) recovering the hemicellulosic monomers as fermentable sugars;

(e) fermenting at least a portion of the fermentable sugars to a fermentation product having a higher normal boiling point than water; and (f) recovering the fermentation product, wherein the process includes process integration of mass and/or energy between at least two of steps (a)-(f).

The present invention also provides one or more products, coproducts, and byproducts produced by a process as described. In preferred embodiments, a product comprises the fermentation product or a derivative thereof. In addition, an intermediate may be produced within a process, and recovered. For example, the intermediate may include purified fermentable sugars in dried form, crystallized form, pressed form, or slurried form.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

Example 1

Cooking of sugarcane straw was conducted with lower ethanol concentration (35 wt %) in mini-reactors of a multi-digester oil bath, compared with previous cooking at higher ethanol concentration (50 wt %). Both cooks were performed at 155° C. for 58 minutes with 12% $SO_2$ at L/W ratio of 4 L/Kg.

Results are summarized in Table 1. The fiber yield as a result of cooking with 35% ethanol is higher than that with 50% ethanol, because more lignin dissolved at higher ethanol content. This is inferred from the lower Kappa number of the cellulose fibers produced at 50% ethanol cooking. Lignin-free yields of fiber produced with 35% and 50% ethanol are 38% and 35%, respectively.

TABLE 1

Composition of sugarcane straw fibers produced with different ethanol concentrations

| | % on od fiber | | | | | | H/(C + H), % |
|---|---|---|---|---|---|---|---|
| ID | Cell | Hemi | Lignin | AcG | UAG | Ash | Hemicellulose |
| 35% EtOH | 78.0 ± 0.8 | 3.9 ± 0.2 | 4.8 ± 0.1 | 0.0 | 1.5 ± 0.3 | 8.5 ± 0.4 | 4.7 |
| 50% EtOH | 82.3 ± 1.3 | 4.5 ± 0.1 | 3.5 ± 0.3 | 0.0 | 1.6 ± 0.3 | 8.4 ± 0.1 | 5.2 |

C: Cellulose;
H: Hemicellulose;
AcG: Acetyl Groups;
UAG: Uronic Acid Groups

Example 2

Cooking of sugarcane straws was conducted in the mini-reactors of a multi digester oil bath. The pulp fibers were produced with subsequent washing and fiber preparation. Design of experiments was followed according to Table 2. The cooking conditions with low ethanol resulted cellulose fibers with low hemicelluloses but relatively high Kappa number. The ethanol:water ratios of 1:4 and 1:3 were able to produce fibers with less than 2% hemicellulosic sugars from sugarcane straw. Also, depending on ethanol concentration of cooking liquor, Kappa number of pulp increases while hemicellulose content does not change much during longer cooking time. Material loss was observed during longer cooking periods.

TABLE 2

Cooking conditions of sugarcane straw and the results

| | Cooking conditions | | | | Results | | | Sugar of fiber | |
|---|---|---|---|---|---|---|---|---|---|
| Run # | Temp (° C.) | Time (min) | $SO_2$ (%) | EtOH:$H_2O$ (w:w) | L/S (w/w) | Yield (%) | Kappa # | Cell. (%) | Hemi. (%) |
| 11 | 160 | 58 | 18 | 1:1 | 6 | 34.3 | 12.6 | 84.1 | 4.1 |
| 17 | 160 | 68 | 18 | 1:1 | 6 | 34.7 | 11.7 | 87.4 | 2.8 |
| 13 | 155 | 58 | 12 | 1:1 | 4 | 38.5 | 14.3 | 84.6 | 5.0 |
| 15 | 155 | 98 | 12 | 1:1 | 4 | 35.4 | 16.6 | 87.7 | 2.3 |
| 14 | 155 | 98 | 12 | 1:1 | 6 | 35.5 | 11.0 | 87.0 | 2.5 |
| 11 | 160 | 58 | 18 | 1:1 | 6 | 34.3 | 12.6 | 84.1 | 4.1 |
| 17 | 160 | 68 | 18 | 1:1 | 6 | 34.7 | 11.7 | 87.4 | 2.8 |
| 18 | 155 | 58 | 12 | 1:2 | 4 | 36.7 | 14.0 | 85.7 | 2.9 |
| 19 | 155 | 58 | 12 | 1:2 | 6 | 36.1 | 13.1 | 86.3 | 3.0 |
| 24 | 155 | 58 | 9 | 1:2 | 4 | 35.9 | 14.3 | 84.1 | 3.6 |
| 22 | 155 | 58 | 12 | 1:2 | 4 | 34.0 | 14.3 | 84.6 | 4.2 |
| 23 | 155 | 58 | 18 | 1:2 | 4 | 37.5 | 14.6 | 84.7 | 3.9 |
| 25 | 155 | 58 | 12 | 1:3 | 4 | 37.0 | 20.1 | 83.5 | 3.3 |
| 26 | 155 | 78 | 12 | 1:3 | 4 | 35.1 | 24.8 | 87.1 | 1.9 |
| 27 | 155 | 98 | 12 | 1:3 | 4 | 34.0 | 26.0 | 82.2 | 2.2 |
| 28 | 155 | 118 | 12 | 1:3 | 4 | 29.5 | 27.0 | 82.6 | 2.1 |
| 20 | 155 | 58 | 15 | 1:3 | 6 | 37.0 | 16.4 | 87.1 | 2.2 |
| 29 | 155 | 58 | 12 | 1:4 | 4 | 37.4 | 22.7 | 82.8 | 3.2 |
| 30 | 155 | 78 | 12 | 1:4 | 4 | 36.1 | 30.3 | 80.7 | 2.2 |
| 31 | 155 | 98 | 12 | 1:4 | 4 | 32.9 | 35.1 | 83.2 | 1.9 |
| 32 | 155 | 118 | 12 | 1:4 | 4 | 33.0 | 40.7 | 79.9 | 1.8 |

What is claimed is:

1. A process for producing an organic aliphatic product from lignocellulosic biomass, said process comprising:
    (a) fractionating a feedstock comprising lignocellulosic biomass in the presence of 10-50 wt % of a solvent for lignin, 3-30 wt % of a hydrolysis catalyst, and water, to produce a liquor containing hemicellulose, cellulose-rich solids, and lignin;
    (b) washing said cellulose-rich solids and separating said cellulose-rich solids from said liquor;
    (c) enzymatically hydrolyzing said cellulose-rich solids to generate a hydrolysate comprising glucose;
    (d) detoxifying said hydrolysate by neutralizing said hydrolysate, removing insoluble solids, and removing or oxidizing residual hydrolysis catalyst, thereby generating a purified hydrolysate;
    (e) fermenting said purified hydrolysate using a suitable microorganism in a fermentor to produce a dilute organic aliphatic product, wherein said microorganism is recycled with a membrane, and wherein said membrane is configured to bleed microorganisms to control cell density in said fermentor;
    (f) extracting said dilute organic aliphatic product into a water-immiscible extractant, to generate an intermediate organic aliphatic product; and
    (g) distilling said intermediate organic aliphatic product to generate a concentrated organic aliphatic product.

2. The process of claim 1, wherein said water-immiscible extractant is selected from the group consisting of methyl ethyl ketone, methyl isobutyl ketone, decanol, dodecanol, oleyl alcohol, butyl butyrate, propionic acid, butyric acid, levulinic acid, succinic acid, and combinations thereof.

3. The process of claim 1, wherein said organic aliphatic product is selected from $C_2$-$C_{12}$ linear or branched alcohols, $C_2$-$C_{12}$ linear or branched acids, $C_2$-$C_{12}$ linear or branched hydrocarbons, and isomers, derivatives, or reaction products, and combinations thereof.

4. The process of claim 1, wherein said organic aliphatic product includes an organic acid selected from the group consisting of formic acid, acetic acid, oxalic acid, lactic acid, propionic acid, 3-hydroxypropionic acid, malonic acid, aspartic acid, fumaric acid, malic acid, succinic acid, glutaric acid, adipic acid, citric acid, itaconic acid, levulinic acid, ascorbic acid, gluconic acid, kojic acid, threonine, glutamic acid, proline, lysine, alanine, serine, and any isomers, derivatives, or combinations thereof.

5. The process of claim 1, wherein said organic aliphatic product includes an oxygenated compound selected from the group consisting of ethanol, propanol, butanol, isopropanol, pentanol, hexanol, heptanol, octanol, glycerol, sorbitol, propanediol, butanediol, butanetriol, pentanediol, hexanediol, acetone, acetoin, butyrolactone, 3-hydroxybutyrolactone, and any isomers, derivatives, or combinations thereof.

6. The process of claim 1, wherein said solvent for lignin comprises a $C_1$-$C_8$ aliphatic or aromatic alcohol.

7. The process of claim 1, wherein said solvent for lignin comprises an aliphatic or aromatic hydrocarbon.

8. The process of claim 1, wherein said solvent for lignin comprises an organic acid.

9. The process of claim 1, wherein said solvent for lignin comprises an inorganic acid.

10. The process of claim 1, wherein said solvent for lignin comprises an ionic liquid.

11. The process of claim 1, wherein said solvent is present in a concentration of about 20 wt % to about 40 wt %.

12. The process of claim 1, wherein said hydrolysis catalyst in step (a) is selected from the group consisting of sulfur dioxide, sulfur trioxide, sulfurous acid, sulfuric acid, sulfonic acid, lignosulfonic acid, elemental sulfur, polysulfides, and combinations or derivatives thereof.

13. The process of claim 12, wherein said hydrolysis catalyst is sulfur dioxide.

14. The process of claim 1, wherein said hydrolysis catalyst is present in a concentration of about 6 wt % to about 20 wt % during step (a).

15. The process of claim 1, wherein step (b) includes countercurrent washing of said cellulose-rich solids to remove said solvent for lignin, said lignin, and said hemicellulose.

16. The process of claim 1, wherein in step (e), fresh microorganisms are propagated into said fermentor along with a nutrient supply to said fermentor.

17. The process of claim 1, wherein steps (f) and (g) are integrated to improve heat recovery.

18. The process of claim 1, wherein step (g) includes recycling distillation bottoms containing enzymes back to step (c).

19. The process of claim 1, said process further comprising hydrolyzing said hemicellulose contained in said liquor to produce hemicellulosic monomers.

20. The process of claim 1, wherein process integration including pinch analysis and energy optimization is performed for each step in said process.

* * * * *